(12) United States Patent
Yoo

(10) Patent No.: US 7,477,835 B2
(45) Date of Patent: Jan. 13, 2009

(54) FOLDABLE WASH WATER STORAGE APPARATUS FOR PORTABLE IRRIGATOR HAVING A TEMPERATURE REGULATION FUNCTION

(76) Inventor: Byung Eun Yoo, 616-5, Daemyeong-9 dong, Nam-gu, Daegu 705-805 (KR)

( * ) Notice: Subject to any disclaimer, the term of this patent is extended or adjusted under 35 U.S.C. 154(b) by 415 days.

(21) Appl. No.: 11/440,256

(22) Filed: May 24, 2006

(65) Prior Publication Data

US 2007/0156120 A1 Jul. 5, 2007

(30) Foreign Application Priority Data

Jan. 2, 2006 (KR) .................. 20-2006-0000052 U

(51) Int. Cl.
*F24H 1/18* (2006.01)
(52) U.S. Cl. ........................ 392/459; 392/441; 604/113; 604/291
(58) Field of Classification Search .................. 604/113, 604/291
See application file for complete search history.

(56) References Cited

U.S. PATENT DOCUMENTS 1,454,388 A * 5/1923 Waldemar .................... 220/9.2
3,058,122 A * 10/1962 McDaniel et al. ............... 4/547

(Continued)

FOREIGN PATENT DOCUMENTS

KR 20-0338146 1/2004

(Continued)

*Primary Examiner*—Thor S Campbell
(74) *Attorney, Agent, or Firm*—Cantor Colburn LLP

(57) ABSTRACT

Disclosed herein is a wash water storage apparatus for portable irrigator that is used to remove feces contained for a long time in the human large intestine or wash the interior of the women's vagina. More particularly, disclosed is a foldable wash water storage apparatus for use with a portable irrigator having a temperature regulation function, which can remove impurities contained in wash water to be supplied into the irrigator while keeping the wash water at a constant temperature, thereby supplying harmless wash water to a human body, and achieving improved convenience in storage and carrying. The wash water storage apparatus for supplying wash liquid such as wash water into a irrigator that is usable to wash the interior of the women's vagina or large intestine and having a temperature regulation function comprises an outer body including a cover configured to close an open upper surface of the outer body and a pair of hanging holes perforated through a rear wall of the outer body, a filtering bucket separably mounted in the outer body and including a filter, and a supporting base mounted below the outer body and including a heater located to come into contact with a lower surface of the filter and adapted to heat wash water having passed through the filtering bucket and a drain pipe to be connected to a wash liquid supply hose of the irrigator. The outer body and filtering bucket are made of the same flexible synthetic resin, respectively and are provided at their corresponding positions with folding lines, respectively, such that the outer body and the filtering bucket seated in the outer body are folded or unfolded together along the folding lines. A power/temperature regulation box is provided at the outside of the outer body. A heater electric wire and sensor wire are connected to both the power/temperature regulation box while being connected to the interior of the supporting base located below the outer body.

4 Claims, 8 Drawing Sheets

U.S. PATENT DOCUMENTS

| | | | | |
|---|---|---|---|---|
| 3,316,882 | A * | 5/1967 | Renwick | 119/269 |
| 3,476,105 | A * | 11/1969 | Abramowitz | 601/162 |
| 3,762,411 | A * | 10/1973 | Lloyd et al. | 604/151 |
| 4,017,915 | A * | 4/1977 | Prewitt | 4/585 |
| 4,201,200 | A * | 5/1980 | Hubner | 601/162 |
| D270,000 | S * | 8/1983 | Ketler | D24/111 |
| 4,622,704 | A * | 11/1986 | Chung | 4/443 |
| 5,030,202 | A * | 7/1991 | Harris | 604/27 |
| D353,891 | S * | 12/1994 | Wadsworth | D24/204 |
| 6,089,394 | A * | 7/2000 | Ziglar | 220/6 |
| RE37,481 | E * | 12/2001 | Crossley et al. | 4/572.1 |
| 6,503,220 | B1 * | 1/2003 | Cirillo et al. | 604/39 |
| 2007/0157956 | A1 * | 7/2007 | Yoo | 134/104.4 |
| 2008/0146991 | A1 * | 6/2008 | Hernandez et al. | 604/34 |

FOREIGN PATENT DOCUMENTS

KR      20-0342570      2/2004

\* cited by examiner

FOLDABLE WASH WATER STORAGE APPARATUS FOR PORTABLE IRRIGATOR HAVING A TEMPERATURE REGULATION FUNCTION

BACKGROUND OF THE INVENTION

1. Field of the Invention

The present invention relates to a foldable wash water storage apparatus for portable irrigator that is used to remove feces contained for a long time in the human large intestine or wash the interior of the women's vagina, and more particularly, to a foldable wash water storage apparatus for portable irrigator having a temperature regulation function, which can remove impurities contained in wash water to be supplied into the irrigator while keeping the wash water at a constant temperature, thereby supplying harmless wash water to a human body, and achieving improved convenience in storage and carrying by virtue of a foldable structure thereof.

2. Description of the Related Art

As well known, the human large intestine has functions of not only regulating the content of moisture and maintaining a predetermined amount of electrolyte, but also making feces from ingesta by bacterial action. However, if the large intestine is not functioning properly, harmful ingredients and poisonous substances are accumulated in the human body, and thus, intestinal paralysis as well as expansion or rupture of aged blood vessels may be caused. As a result, the large intestine may be a hotbed of bacteria and various intestinal diseases such as constipation, diarrhea, indigestion, slim feces, abdominal intumescence, large intestine cancer, colitis, anaphylaxis, ulcer of the large intestine, piles, etc.

Accordingly, since accumulation of waste materials in the intestines causes intestinal paralysis, malfunction of the intestines, skin aging, and other various diseases, there is the urgent need for appropriate measures to eliminate the causes of the various intestinal diseases. For this reason, conventional, intestinal irrigators have been used to remove the waste materials in the intestines and consequently prevent the various intestinal diseases. The conventional intestinal irrigators have been found to obtain outstanding effects in the removal of poisonous substances caused by feces contained for a long time in the large intestine, and therefore, are being widely used for the prevention and treatment of various intestinal diseases.

As an example of the conventional intestinal irrigators, Korean Utility Model Registration Nos. 338,146 and 342,570, which are registered by the applicant of the present invention, disclose portable irrigators having advantages of simple and convenient use with no cumbersome use feeling. However, the disclosed portable irrigators have problems in that a water container, in which wash water to be supplied into the irrigator is received, has a poor outer appearance and also is undesirable in view of sanitation because it has no function of preventing invasion of impurities into the received wash water.

Furthermore, the disclosed container has a problem of inconvenience in use, and is unsuitable for use as a portable container.

SUMMARY OF THE INVENTION

Therefore, the present invention has been made in view of the above problems, and it is an object of the present invention to provide a foldable wash water storage apparatus for portable irrigator used by a patient or woman for the washing of the large intestine or women's vagina, which can remove impurities contained in wash water to be supplied into the irrigator while appropriately regulating the temperature of the wash water, and can be wholly folded and unfolded so as to achieve an increased convenience in carrying and storage.

In accordance with the present invention, the above and other objects can be accomplished by the provision of a foldable wash water storage apparatus for supplying wash liquid such as wash water into a portable irrigator that is usable to wash the interior of the women's vagina or large intestine, the foldable wash water storage apparatus having a temperature regulation function, comprising: an outer body including a cover configured to close an open upper surface of the outer body and a pair of hanging holes perforated through a rear wall of the outer body; a filtering bucket separably mounted in the outer body and including a filter; and a supporting base mounted below the outer body and including a heater located to come into contact with a lower surface of the filter and adapted to heat wash water having passed through the filtering bucket and a drain pipe to be connected to a wash liquid supply hose of the irrigator, wherein the outer body and filtering bucket are made of the same flexible synthetic resin, respectively and are provided at their corresponding positions with folding lines, respectively, such that the outer body and the filtering bucket seated in the outer body are folded or unfolded together along the folding lines, and wherein a power/temperature regulation box is provided at the outside of the outer body, and a heater electric wire and sensor wire are connected to both the power/temperature regulation box and the interior of the supporting base located below the outer body.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Now, preferred embodiments of the present invention will be explained in detail with reference to the accompanying drawings.

Figure 1:
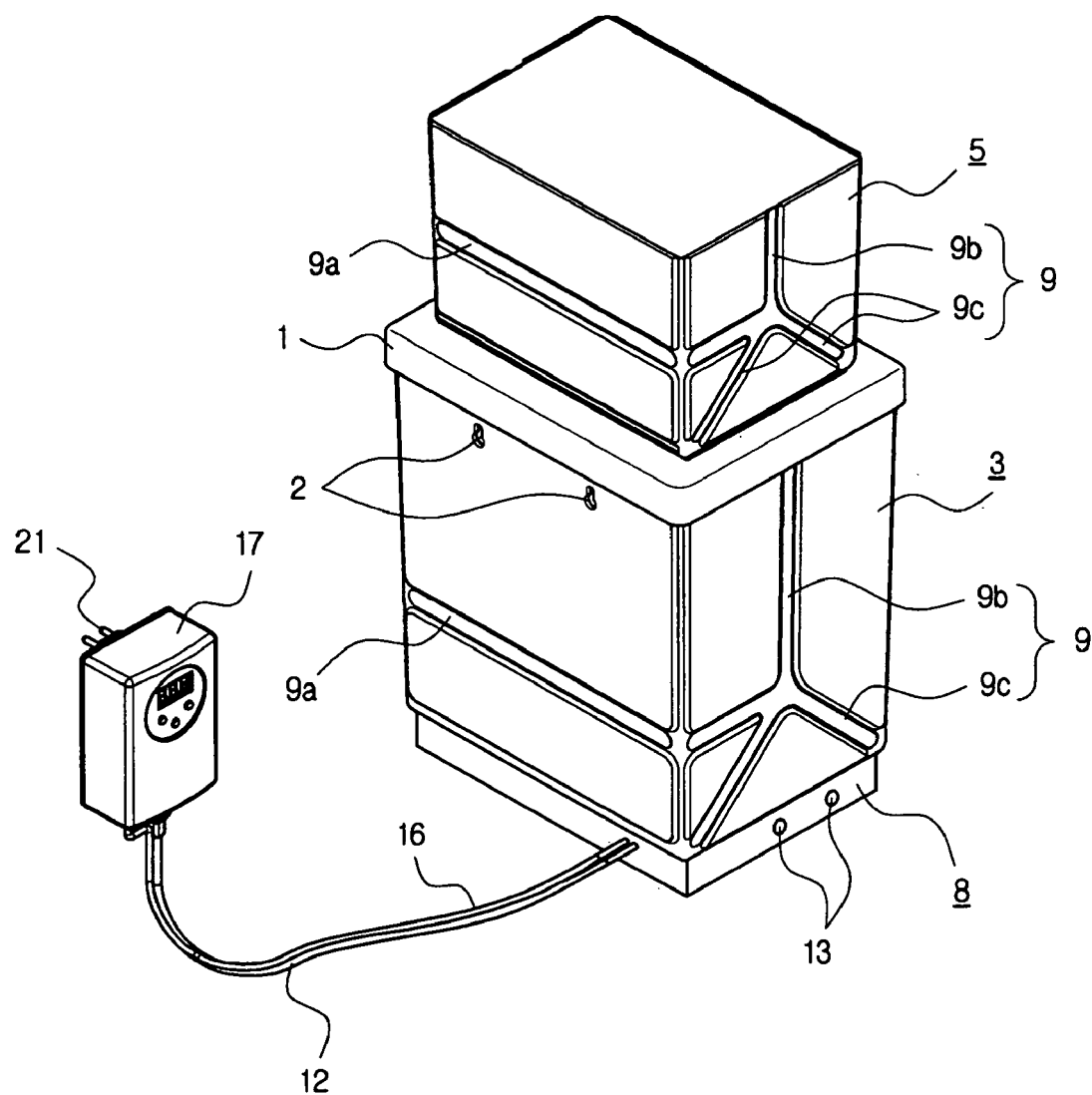
FIG. 1 is a rear perspective view illustrating a foldable wash water storage apparatus for portable irrigator having a temperature regulation function according to the present invention.
Figure 2:
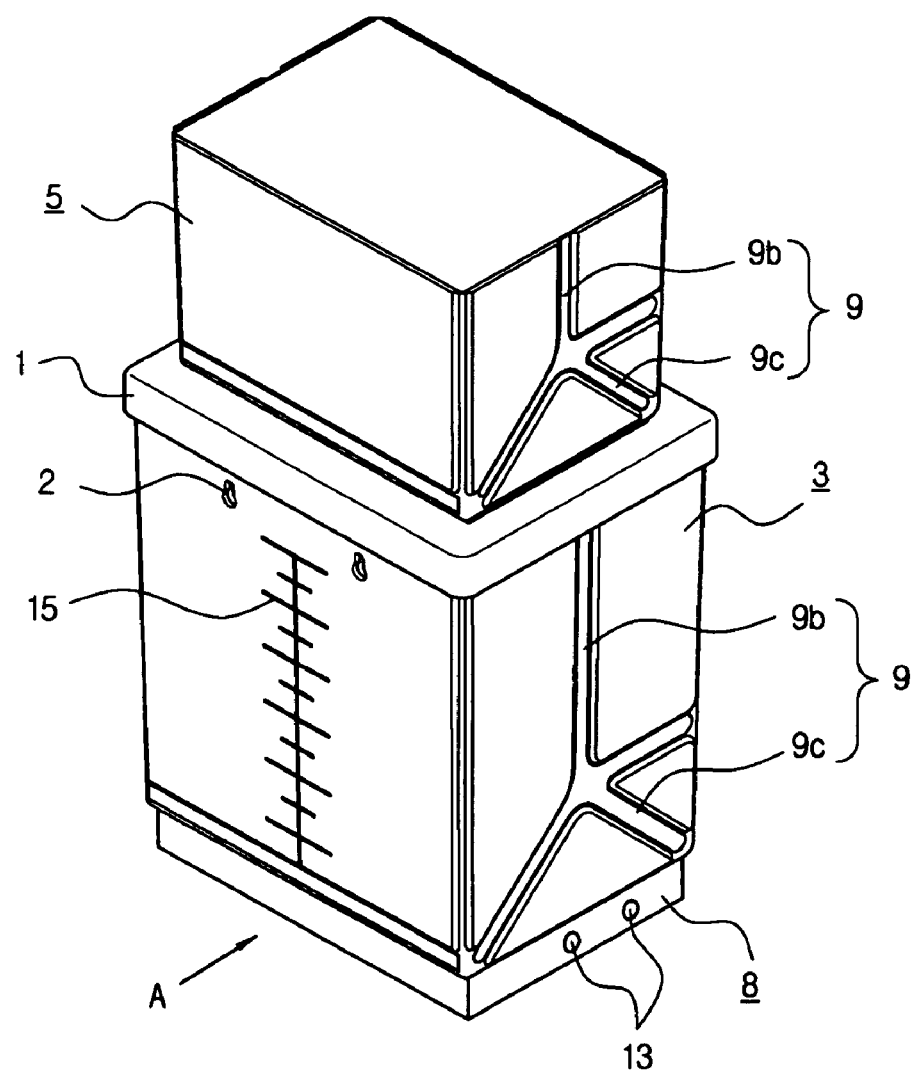
FIG. 2 is a front perspective view of the foldable wash water storage apparatus according to the present invention.
Figure 3:
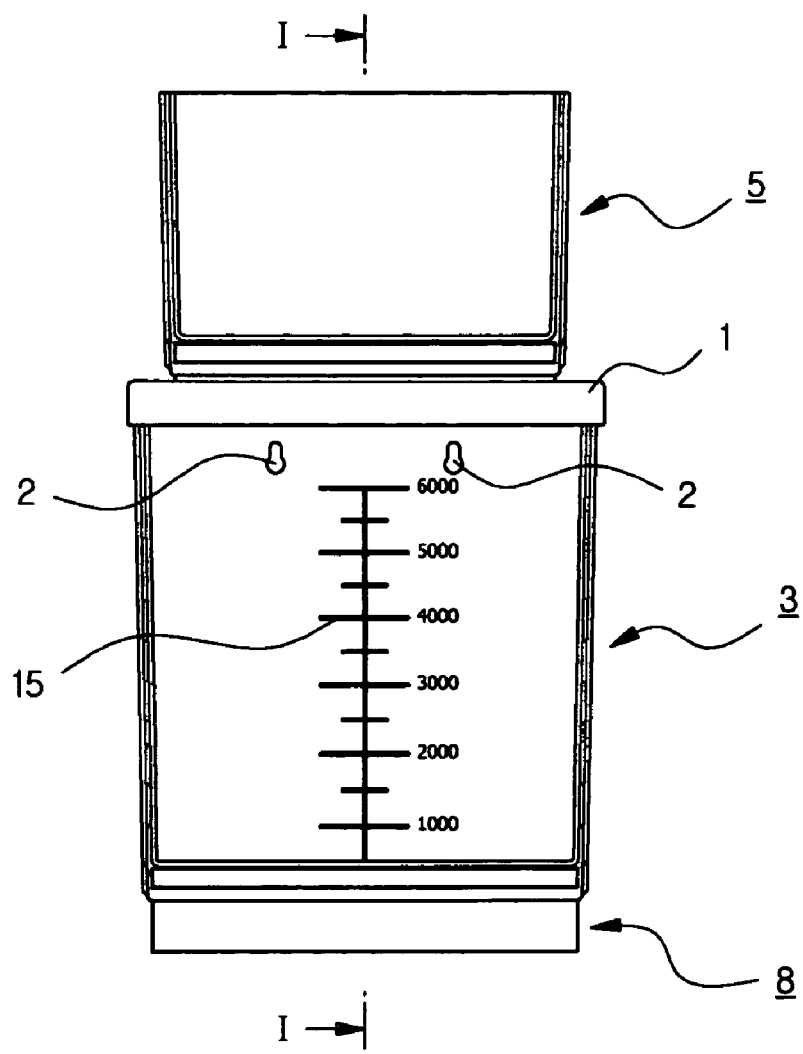
FIG. 3 is an elevation view of the foldable wash water storage apparatus according to the present invention, when viewed from the direction A of FIG. 2.
Figure 4:
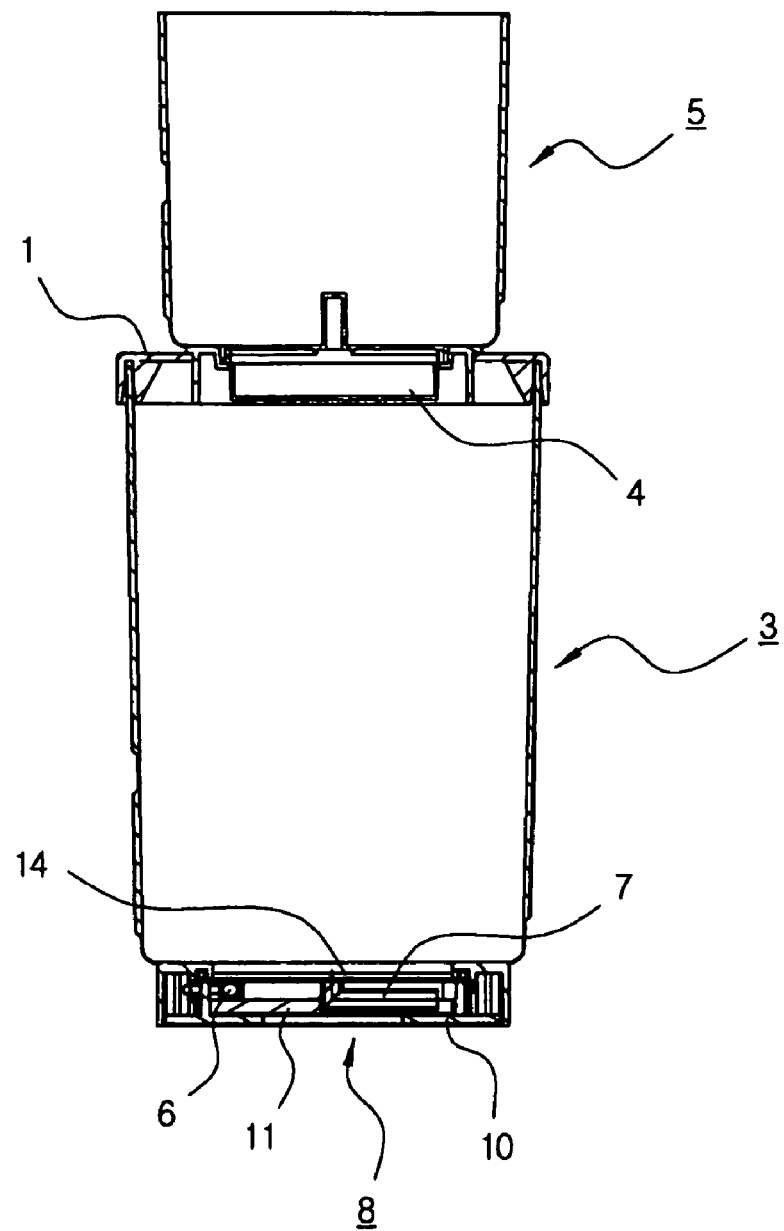
FIG. 4 is a sectional view taken along the line I-I of FIG. 3.

FIGS. 1 and 2 are perspective views illustrating a state wherein a filtering bucket is lifted from a foldable wash water storage apparatus having a temperature regulation function according to the present invention. FIG. 3 is an elevation view of the foldable wash water storage apparatus, when viewed from the direction A of FIG. 2. FIG. 4 is a sectional view taken along the line A-A of FIG. 3.

The wash water storage apparatus of the present invention is used to supply wash liquid such as wash water into a irrigator 100 that is usable to wash the interior of the women's vagina or large intestine. The wash water storage apparatus basically includes an outer body 3, a filtering bucket 5, and a supporting base 8. More particularly, the outer body 3 includes a cover 1 configured to close an open upper surface of the outer body 3. A pair of hanging holes 2 are perforated through a rear wall of the outer body 3. The filtering bucket 5 is separably mounted in the outer body 3, and includes a filter 4. The supporting base 8, which is mounted below the outer body 3, includes a heater 6 installed to come into contact with a lower surface of the filter 4 and adapted to heat wash water having passed through the filtering bucket 5, and a drain pipe 7 to which a wash liquid supply hose 101 of the irrigator 100 will be connected. The outer body 3 and filtering bucket 5 are made of the same flexible synthetic resin, respectively. Also, the outer body 3 and filtering bucket 5 are provided at their corresponding positions with folding lines 9, respectively. With this configuration, in a state wherein the filtering bucket 5 is inserted into and seated in the outer body 3, the outer body 3 and filtering bucket 5 are able to be folded or unfolded together along the folding lines 9. A power/temperature regulation box 17 is provided at the outside of the outer body 3. A heater electric wire 12 and sensor wire 16 are connected to the power/temperature regulation box 17 while being connected to the interior of the supporting base 8 located below the outer body 3.

In the present invention, the folding lines 9, which are formed at the outer body 3 and filtering bucket 5, consist of horizontal folding lines 9a, vertical folding lines 9b, and branch folding lines 9c connected to the vertical folding line 9b.

The supporting base 8 mounted below the outer body 3 further includes a hard case 10 defining the outer appearance of the supporting base 8, and an insulation material 11 attached to an inner wall surface of the hard case 10 to surround a temperature sensor 18, bimetal 19, water level sensor 20, and the heater 6. Also, the hard case 10 of the supporting base 8 is perforated through opposite side walls thereof with heat discharge holes 13 for discharging heat generated from the heater 6, connected to the heater electric wire 12, to the outside. In the present invention, the outer body 3 is mounted in a bottom surface thereof with a silver plate 14 for sterilizing harmful bacteria having passed through the filter 4, and the heater 6 is located below the silver plate 14.

The sensor wire 16 and heater electric wire 12 are connected to the temperature sensor 18, bimetal 19, and water level sensor 20 mounted in the supporting base 8 while being connected to the power/temperature regulation box 17 having a power plug 21. The power/temperature regulation box 17 also has a power switch 22, temperature raising and lowering switches 23, and a temperature gauge window 24 used to display a temperature setting state.

The outer body 3 is formed at a front outer wall surface thereof with a water level scale 15 for measuring the amount of wash water filled in the filtering bucket 5 when the filtering bucket 5 is inserted and seated in the outer body 3. The hanging holes 2 of the outer body 3 are formed at positions close to an upper rim of the outer body 3 such that the outer body 3 can be hung on hooks of a separate fixing rack in use of the foldable water storage apparatus of the present invention.

Figure 5:
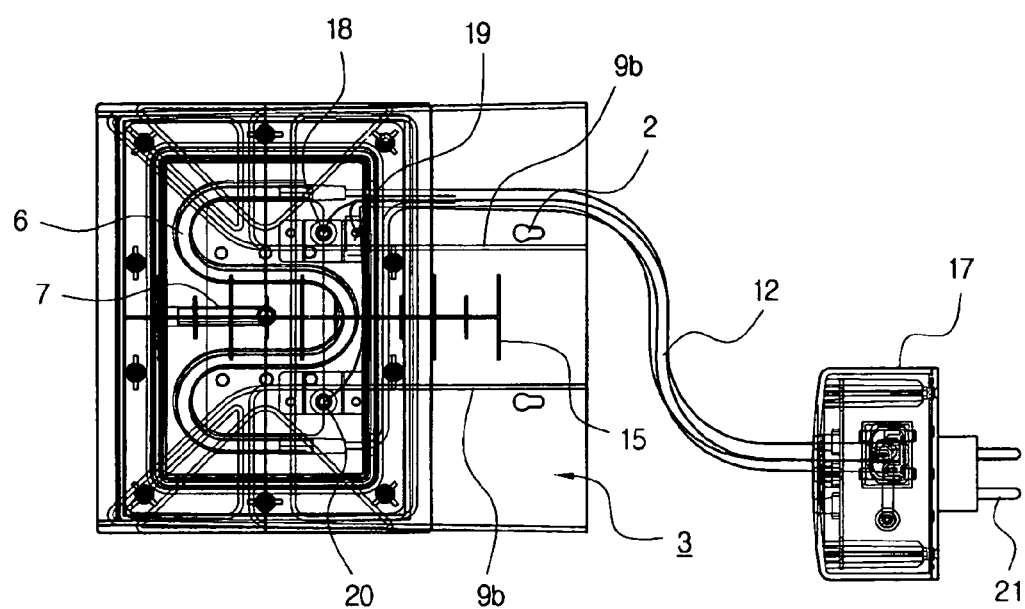
FIG. 5 is a top plan view illustrating a folded state of the foldable wash water storage apparatus according to the present invention.
Figure 6:
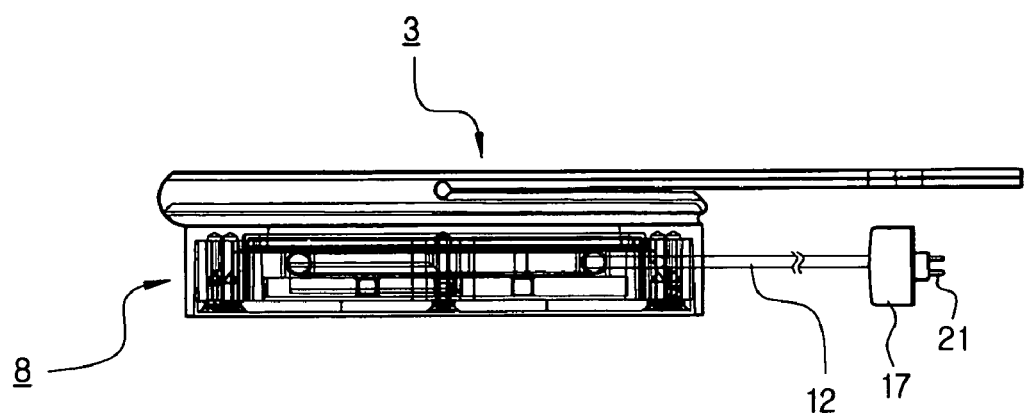
FIG. 6 is a side view of FIG. 5.
Figure 7:
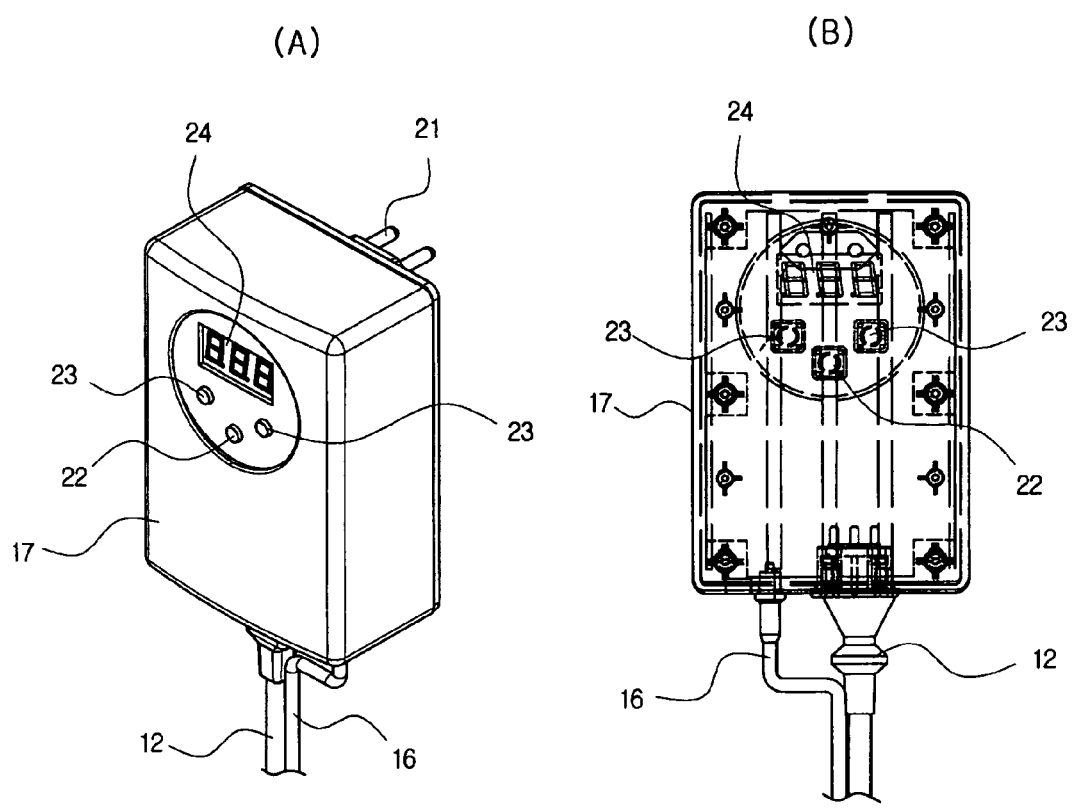
FIGS. 7A and 7B are an enlarged perspective view and a sectional view, respectively, illustrating a power/temperature regulation box according to the present invention.

FIGS. 5 and 6 illustrate a folded state of the water storage apparatus according to the present invention. For this, first, the filtering bucket 5 is inserted into the outer body 3, and both the filtering bucket 5 and outer body 3 are folded together along the folding lines 9 thereof.

Figure 8:
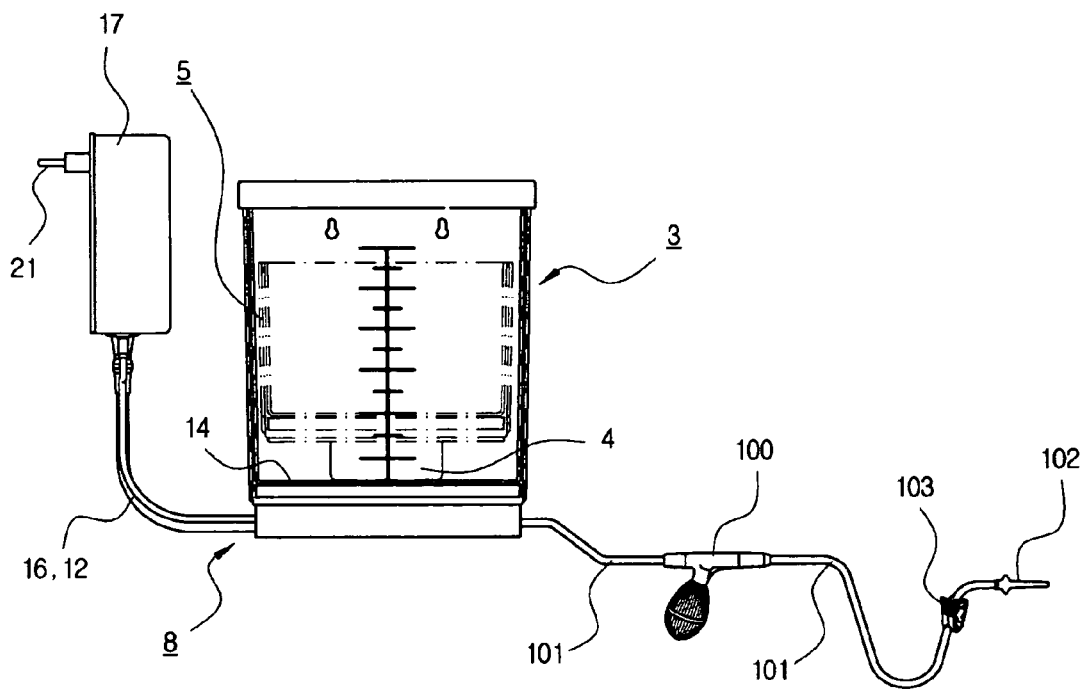
FIG. 8 is a view illustrating the use example of the present invention.

FIG. 8 illustrates the use example of the present invention. In use, first, the filtering bucket 5, which is filled with wash water, is received in the outer body 3, and the wash liquid supply hose 101 of the conventional portable irrigator 100 is connected to the drain pipe 7 mounted in the supporting base 8. Then, if the power switch 22 of the power/temperature regulation box 17 is turned on to supply power to the heater 6 while simultaneously setting an appropriate temperature by use of the temperature raising and lowering switches 23, the heater 6 operates to heat the wash water having passed through the filtering bucket 5 to the set appropriate temperature. Thereafter, the heated wash water is supplied into the irrigator 100 by way of the drain pipe 7 and wash liquid supply hose 101, and subsequently, supplied into the interior of the intestine or women's vagina through a nozzle 102 in accordance with pumping operations of the irrigator 100. In this case, the flow rate of wash water being supplied through the wash liquid supply hose 101 is able to be regulated by use of a flow rate regulator 103 coupled to the wash liquid supply hose 101.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A foldable wash water storage apparatus for supplying wash liquid such as wash water into a portable irrigator that is usable to wash the interior of the women's vagina or large intestine, the foldable wash water storage apparatus having a temperature regulation function comprising an outer body including a cover configured to close an open upper surface of the outer body and a pair of hanging holes perforated through a rear wall of the outer body, a filtering bucket separably mounted in the outer body and including a filter, and a supporting base mounted below the outer body and including a heater located to come into contact with a lower surface of the filter and adapted to heat wash water having passed through the filtering bucket and a drain pipe to be connected to a wash liquid supply hose of the irrigator, characterized in that the outer body and filtering bucket are made of the same flexible synthetic resin, respectively and are provided at their corresponding positions with folding lines, respectively, such that the outer body and the filtering bucket seated in the outer body are folded or unfolded together along the folding lines, and a power/temperature regulation box is provided at the outside of the outer body, and a heater electric wire and sensor wire are connected to both the power/temperature regulation box and the interior of the supporting base located below the outer body.

2. The apparatus as set forth in claim 1, wherein the folding lines, which are formed at the outer body and filtering bucket, consist of horizontal folding lines, vertical folding lines, and branch folding lines connected to the vertical folding lines.

3. The apparatus as set forth in claim 1, wherein the supporting base mounted below the outer body further includes:

a hard case defining the outer appearance of the supporting base;

an insulation material attached to an inner wall surface of the hard case to surround a temperature sensor, bimetal, water level sensor, and the heater received in the hard case; and
a plurality of heat discharge holes perforated through opposite side walls of the hard case for discharging heat generated from the heater, connected to the heater electric wire, to the outside,
wherein the outer body is mounted in a bottom surface thereof with a silver plate, and the heater is located below the silver plate.

4. The apparatus as set forth in claim 1,
wherein the sensor wire and heater electric wire are connected to the temperature sensor, bimetal, and water level sensor received in the supporting base while being connected to the power/temperature regulation box, and
wherein the power/temperature regulation box has a power plug, a power switch, temperature raising and lowering switches, and a temperature gauge window used to display a temperature setting state.

* * * * *